United States Patent
Gonzales et al.

(10) Patent No.: US 10,286,093 B2
(45) Date of Patent: May 14, 2019

(54) METHOD OF DIAGNOSING AND TREATING ALZHEIMER'S DISEASE

(71) Applicants: Nigel R. Steveson, Sugar Hill, GA (US); Gilbert R. Gonazles, Tucson, AZ (US)

(72) Inventors: Gilbert R. Gonzales, Tucson, AZ (US); Nigel R. Stevenson, Sugar Hill, GA (US)

(73) Assignee: NeuroSn, Inc., Tucson, AZ (US)

( * ) Notice: Subject to any disclaimer, the term of this patent is extended or adjusted under 35 U.S.C. 154(b) by 172 days.

(21) Appl. No.: 14/891,835

(22) PCT Filed: May 21, 2014

(86) PCT No.: PCT/US2014/038933
§ 371 (c)(1),
(2) Date: Nov. 17, 2015

(87) PCT Pub. No.: WO2014/190030
PCT Pub. Date: Nov. 27, 2014

(65) Prior Publication Data
US 2016/0101198 A1  Apr. 14, 2016

Related U.S. Application Data

(60) Provisional application No. 61/826,701, filed on May 23, 2013.

(51) Int. Cl.
*A61K 51/00* (2006.01)
*A61M 36/14* (2006.01)
*A61K 51/08* (2006.01)

(52) U.S. Cl.
CPC .......... *A61K 51/087* (2013.01); *A61K 51/088* (2013.01)

(58) Field of Classification Search
CPC ........ A61K 38/00; A61K 51/00; A61K 51/08; A61K 51/087; A61K 51/088; A61K 2121/00; A61K 2123/00; A61K 2300/00
USPC .......... 424/1.11, 1.65, 1.69, 1.81, 1.85, 1.89, 424/9.1, 9.2, 9.3, 9.4, 9.5, 9.6; 530/300; 514/1, 1.1
See application file for complete search history.

(56) References Cited

U.S. PATENT DOCUMENTS 6,197,278 B1 * 3/2001 Blankenberg .......... A61B 6/037 424/1.11
8,283,167 B2 * 10/2012 Simon ................... A61K 51/088 435/173.9

2010/0166653 A1  7/2010 Stevenson et al.
2010/0204457 A1  8/2010 Simon
2011/0177002 A1  7/2011 Zitzmann-Kolbe et al.

OTHER PUBLICATIONS

Peri et al, Cell, 2008, vol. 133, pp. 916-927.*
Neniskyte et al: "Neuronal Death Induced by Nanomolar Amyloid is Mediated by Primary Phagocytosis of Neurons by Microglia", Journal of Biological Chemistry, vol. 286, No. 46, Nov. 18, 2011 (Nov. 18, 2011), pp. 39904-39913, XP055134581, ISSN: 0021-9258, DOI: 10.1074/jbc.M111.267583.
Stevenson Nigel et al: "Production and applications of very high specific activity Sn-117m and labeled chelates/molecules", Journal of Labelled Compounds and Radiopharmaceuticals, vol. 56, No. Supplement 1 May 9, 2013 (May 9, 2013), p. S40, XP008171213, ISSN: 0362-4803, DOI: 10.1002/JLCR.3057 Retrieved from the Internet: URL:http://onlinelibrary.wiley.com/doi/10.1002/jlcr.3057/pdf [retrieved on Aug. 12, 2014].
Lahorte C M M et al: "Apoptosis-Detecting Radioligands: Current State of the Art and Future Perspectives", European Journal of Nuclear Medicine and Molecular Imaging, Springer Verlag, Heidelberg, DE, vol. 31, No. 6, Jun. 1, 2004 (Jun. 1, 2004), pp. 887-919, XP008064142, ISSN: 1619-7070, DOI: 10.1007/S00259-004-1555-4.
S. McArthur et al: "Annexin A1: A Central Player in the Anti-Inflammatory and Neuroprotective Role of Microglia", The Journal of Immunology, vol. 185, No. 10, Oct. 20, 2010 (Oct. 20, 2010), pp. 6317-6328, XP055134640, ISSN: 0022-1767, DOI: 10.4049/jimmunol.1001095.
Egle Solito et al: "Microglia Function in Alzheimer's Disease", Frontiers in Pharmacology, vol. 3, Feb. 1, 2012 (Feb. 1, 2012), XP055134645, DOI: 10.3389/fphar.2012.00014.
Written Opinion/IPR from corresponding PCT application No. PCT/US2014/038933, international filing date May 21 2014, priority date May 23, 2013, dated Dec. 3, 2015 (13 pages).

* cited by examiner

*Primary Examiner* — D. L. Jones
(74) *Attorney, Agent, or Firm* — Wood Herron & Evans LLP

(57) ABSTRACT

Alzheimer's disease is treated by attacking hyperactive microglia preferably before excessive beta amyloid is built up by administering tin-117m-DOTA annexin V. This compound in low radioactive doses selectively binds to the aged hyperactive microglia and emits a conversion electron which effectively induces apoptosis in the hyperactive microglia. A follow-up treatment of tin-annexin A1 can be administered to repair the blood brain barrier. The annexin A1 assists in the repair of the blood-brain barrier and the associated tin-117m will induce apoptosis in aged hyperactive microglia associated with the blood brain barrier.

5 Claims, 1 Drawing Sheet

US 10,286,093 B2

METHOD OF DIAGNOSING AND TREATING ALZHEIMER'S DISEASE

PRIORITY CLAIM

This application is based on, and claims priority to, U.S. provisional patent application Ser. No. 61/826,701, filed May 23, 2013, the disclosure of which is hereby incorporated by reference in its entirety as if fully set forth herein.

BACKGROUND OF THE INVENTION

There are various theories on the causes and development of Alzheimer's disease. But, it is very clear that it involves a build-up of beta amyloid with subsequent deterioration of cognitive ability.

The beta amyloid is formed from microglia, which are the macrophages of the brain. Microglia have several important functions in the brain. However, the microglia can become hyperactive and, as a result, cause the production and build-up of beta amyloid in the brain, which subsequently causes cognitive deterioration. Generally, most of the beta amyloid is produced prior to any clinical detection of even mild cognitive impairment. By the time of diagnosis, up the 50% of the brain mass may have been lost. Thus, any treatment of Alzheimer's should occur prior to the onset of dementia and, preferably, much earlier.

Further, as with most neurodegenerative diseases, there is also a deterioration of the blood brain barrier.

SUMMARY OF THE INVENTION

The present invention is premised on the realization that the build-up of beta amyloid can be inhibited by destroying the aged hyperactive microglia. Hyperactive microglia can be destroyed by binding a short range radioactive isotope only to the aged hyperactive microglia. This will cause a destruction of the aged hyperactive microglia by induction of apoptosis in these microglia, preventing them from participating in the cascade of events that produces beta amyloid. In particular, the present invention utilizes tin-117m as a radionuclide to attach to the hyperactive microglia, and in particular, tin-117m-annexin V.

In a further embodiment of the present invention, a second dosage of tin-117m attached to annexin A1 can be administered. The annexin A1 assists in repair of the blood brain barrier, and the tin-117m in turn destroys any hyperactive microglia and other inflammatory immune reactive cells associated with the deterioration of the blood-brain barrier.

The objects and advantages of the present invention will be further appreciated in light of the following detailed description.

DETAILED DESCRIPTION

Figure 1:
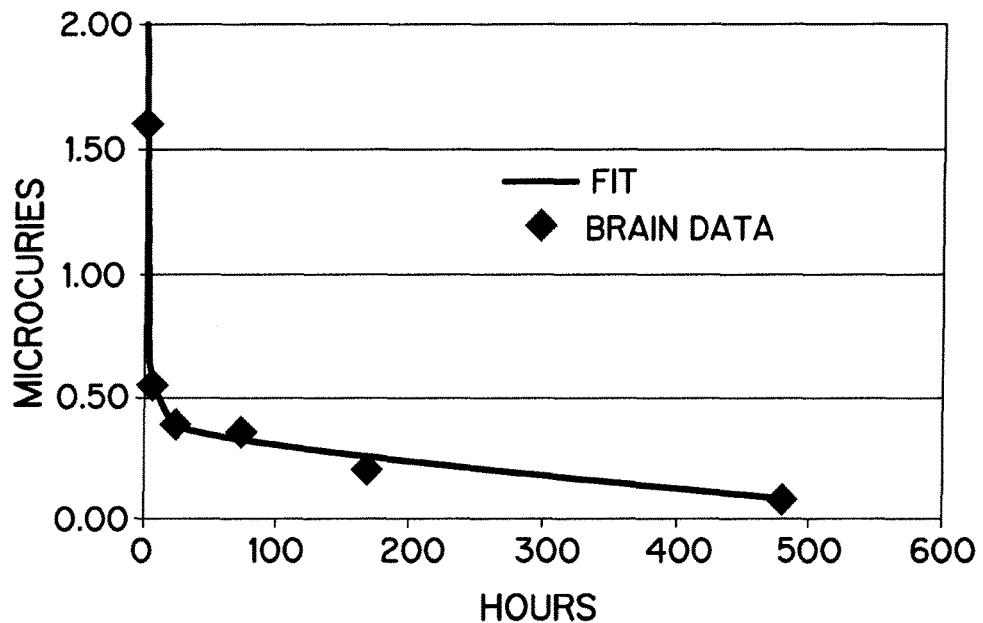
FIG. 1 is a graph of data showing the observed dosage in brain over time after a peripheral injection of a composition in accordance with embodiments of the invention.

According to the present invention, Alzheimer's disease is treated by administering to a patient an amount of a tin-annexin V effective to induce apoptosis of hyperactive microglia cells.

The tin-117m annexin is preferably formed from no-carrier-added tin-117m. There are various methods to produce no-carrier added tin-117m. One such method is disclosed in Stevenson U.S. Pat. No. 8,257,681, the disclosure of which is hereby incorporated by reference, although other methods could be employed in the present invention. The tin-117-m is a unique radioisotope. Although it emits some gamma radiation, the primary source of the radiation is a conversion electron. The radiation from the conversion electron penetrates a set distance, 290 microns, and, therefore, does not damage cells any farther than 290 microns away from the tin atom.

In an embodiment, the radionuclide is a high specific activity ("HSA") tin-117m. In an exemplary embodiment, the HSA tin-117m has a specific activity of greater than 100 Ci/g. In another exemplary embodiment, the HSA tin-117m has a specific activity may range from 500 Ci/g to 25,000 Ci/g. In another exemplary embodiment, the HSA tin-117m has a specific activity may range from 800 Ci/g to 20,000 Ci/g. In yet another exemplary embodiment, the HSA tin-117m has a specific activity may range from 1,000 Ci/g to 5,000 Ci/g.

The tin-117m in turn is bonded to an annexin molecule. Annexins are a class of molecule having the ability to bind with high affinity to membrane lipids in the presence of millimolar concentrations of calcium. There are several different annexins. The term "annexin" includes native annexin purified from natural sources, such as human placenta or annexin molecules containing a native sequence produced through, for example, genetic engineering, or other means. The term annexin unless otherwise specified, includes annexins as defined below derived from or produced by any source.

Modified annexin is a molecule with a native sequence of molecules altered in such a way without materially altering the membrane binding affinity of the annexin. Such annexins can be produced by chemical, genetic engineering or recombinant techniques as known to those of ordinary skill in the art. The modification can include a modification of the sequence through the addition of several amino acid residues and/or an addition/deletion of amino acids at a single site of the native or genetically engineered sequence. For example, the annexin can be modified at the N-terminus by addition of amino acid residues wherein at least one of its amino acids provide an accessible sulfhydryl group. The accessible sulfhydryl group or groups may be utilized during conjugation or remain available for further conjugation. The term "modified annexin" includes annexin multimers.

Annexin multimers are a combination of two or more monomeric modified annexin molecules of which the components of the multimer may be native, or recombinant, or in any combination thereof resulting in similar or improved membrane binding affinity over the monomeric annexin. A multimer composed of up to 20 modified annexins is useful in the present invention. One example of an annexin multimer is an annexin dimer, which can be composed of two modified annexins linked by disulfide bonds between accessible cysteine groups on the modified annexins. The annexin dimer can also be produced directly as a fusion protein.

Typically a linking molecule is used to attach the tin-117m to the annexin. One such linking molecule is 1,4,7,10-tetraazacyclododecane-1,4,7,10-tetraacetic acid, or DOTA. Usually, aminobenzyl DOTA is used. Formation of this molecule is disclosed in U.S. Pat. No. 8,283,167, the disclosure of which is hereby incorporated by reference. As discussed below, annexin V is preferably used to bind and destroy hyperactive microglia through induction of apoptosis. Annexin A1 is used to repair the blood brain barrier.

Alzheimer's disease is treated by administering an effective dosage of tin-117m annexin V generally linked together with DOTA. The dosage utilized in the present invention will vary depending upon the mode of administration. The tin-117m annexin V in a suitable carrier, such as saline, can be administered intra-arterially, intra-spinally, including in the lumbar, or intra-cisternally, intra-vascularly, or directly into the ventricle of the brain. The more direct the path to the brain for the tin-117m, the lower the requisite dosage. Preferably, it is desirable to apply a dosage which is sufficient to provide conversion electron therapy in the brain at a hormetic dosage. Generally a much lower dosage provides hormesis, generally around 0.03 to 0.3 millicuries to each hemisphere of the brain. However, the systemic injected dosage can vary widely and can be from about 3 millicuries up to 50 millicuries, generally about 3 millicuries to about 20 millicuries or 5 to 10 millicuries.

The hyperactive microglia has exposed phosphatidyl serine to which the annexin naturally binds. This binds the tin-117m to the hyperactive microglia. Because tin-117m only has a therapeutic energy in the form of conversion electrons that travels 290 microns and that in low therapeutic doses (i.e., non-DNA fracturing doses or hormesis doses), when attached to the microglia the radiation will mainly affect interneuronal areas in the brain where aged microglia are located.

The timing of administration should be as early as possible, and can, in fact, occur prior to any clinical signs of Alzheimer's. Administration of tin-117m annexin V is warranted as soon as there is any indication of beta amyloid build-up, tauprotein formation, or other potential changes associated with Alzheimer's disease Because the build-up of beta amyloid precedes clinical signs of Alzheimer's by years, certainly as soon as any clinical signs of Alzheimer's are detected, the composition of the present invention should be administered. The tin-117m annexin V can be readministered. As the tin-117 remains in the brain for extended periods of time, well in excess of 400 hours, one should wait at least one to two half lives before readministering the tin-117m. The tin-117m annexin can be readministered two or more times, generally for the remainder of the patient's life at 3-month to 1-year intervals. Likewise, the tin-117m annexin A1 can b readministered at the same intervals.

EXAMPLE 1

Establishing the efficacy of the present invention, 500 microcuries of tin-117m bonded to DOTA annexin V were injected into a peripheral vein of a patient as shown in the Figure. Initially, the observed dosage in brain was 1.5 microcuries, which quickly dropped off to .5 microcuries, and stabilized at between .4 and .1 microcuries over a period of over 400 hours. This demonstrates that the tin DOTA annexin crossed the blood brain barrier, localized in the brain, and remained effective in the brain over an extended period of time. The noted decrease over 400 hours would be expected due to the half-life of the tin-117m, which is 14 days. (See FIG. 1.)

A second therapeutic compound, tin-117m annexin A1 (tin-117m aminobenzyl DOTA annexin A1) can be administered at the same approximate dosage as the tin annexin V. The annexin A1 will help repair the blood brain barrier, which is normally in disrepair in individuals with Alzheimer's, and the associated tin-117m will induce apoptosis in aged hyperactive microglia present.

The tin-117m-annexin A1 complex can be administered at the same time as the tin-117m-annexin V complex, but preferably, one should wait approximately one half of the half life of the tin (or 7 days), up to about two half lives (or 28 days) before administering the tin-117m-annexin A1, so that the tin-117m-annexin A1 does not interfere with the tin-117m annexin V crossing the blood brain barrier.

EXAMPLE 2

Figure 2:
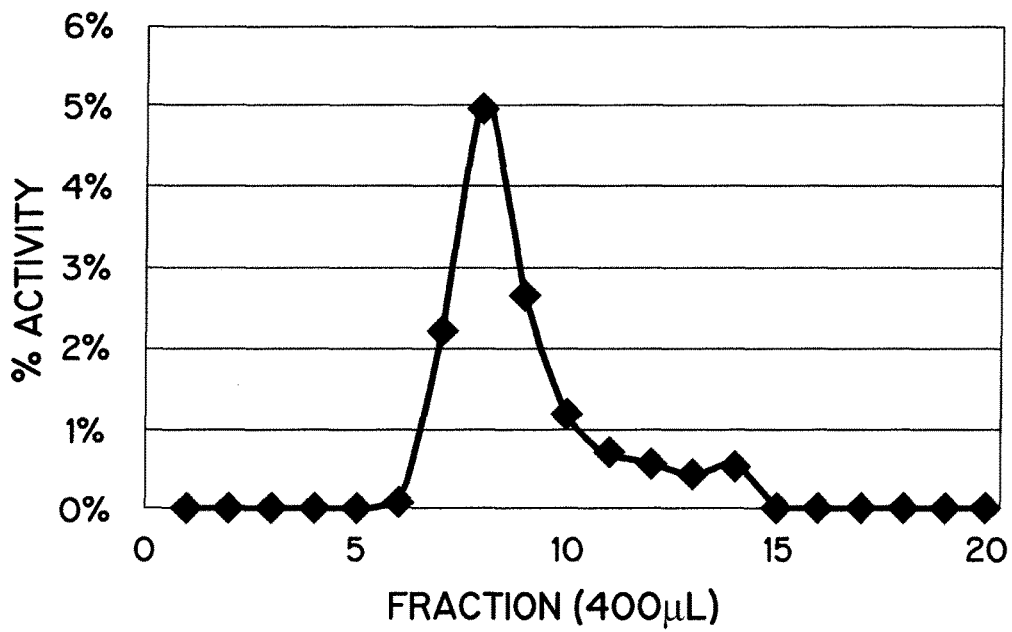
FIG. 2 is a graph of data collected during purification of Sn-117m-Annexin A-, in accordance with embodiments of the invention.

One mCi of Sn-117m dissolved in 4 M HCl with a specific activity of 4,659 Ci/g was placed in a vial and evaporated to dryness. An aqueous solution f a bifunctional chelating agent, aminobenzyl-DOTA, was added at a 10:1 ratio of chelant to total metal in solution. The solution was sealed and heated at 140° C. for 15 minutes. The Sn-117m-DOTA chelate formed was purified by reverse phase HPLC to remove excess chelant and other impurities in the sample. The resultant purified chelate was treated with 0.2 microliters of neat thiophosgene and the excess thiophosgene was removed by three extractions with ether. This resulted in the conversion of the aniline group into an isothiocyanato group. The pH of the chelate was adjusted to about then 0.37 mg of Annexin V in 0.367 microliters was added. The pH was adjusted to 9.2 with bicarbonate buffer and the solution was heated while rocking at 37° C. for one 90 minutes. The contents of the vial were purified using a 10 mL gravity fed desalting column (Bio-Rad EconoPac-10DG) and 0.5 mL fractions were collected. The product peak containing Sn-117m-Annexin A-1 (also referred to as lipocortin) eluted in fractions 7-10 (FIG. 2). The yield based on the Sn-117m activity was 12%.

In another embodiment of the present invention, the tin-117m-annexin-V can be used as a diagnostic tool to determine the presence of hyperactive microglia by administering the tin-117m-DOTA annexin V and imaging the brain. The tin-117m emits gamma radiation, which can be detected by SPECT. Alternately, a compound such as Tc-99m annexin V can be utilized purely for diagnostic purposes. Greater than normal radiation detected in the brain is indicative of Alzheimer's disease even prior to cognitive impairment.

Thus, according to the present invention, Alzheimer's disease can be detected and/or treated at a very early stage by destroying hyperactive microglia cells before massive build-up of beta amyloid and the associated loss of brain mass and cognitive ability. The present invention allows for a method of detecting the hyperactive microglia at a very early stage, and provides a specific mode of attacking the hyperactive microglia. Because a relatively low dosage is required, a hormesis affect is achieved. Further, because of the short effective distance of the emitted radiation from the tin-117m, only white matter is affected and the grey matter, or neurons of the brain, are not adversely impacted by the present therapy. This can be repeated as needed, as the compound has minimal, if any, deleterious effect. Further, the present invention provides the added benefit of being able to repair the blood brain barrier.

This has been a description of the present invention along with the preferred method of practicing the present invention. However, the invention itself should only be defined by the appended claims.

What is claimed is:

1. A method of detecting microglia having exposed phosphatidyl serine comprising administering to a patient annexin V labeled with a detectable radionuclide at a dose sufficient to bind to exposed phosphatidyl serine on the microglia in said patient's brain and noninvasively detecting said radionuclide bound to exposed phosphatidyl serine on the microglia in the brain of said patient, wherein the radionuclide is tin-117m having a specific activity between 500 Ci/g and 25,000 Ci/g at the end of bombardment.

2. The method of claim 1 wherein said radionuclide in the brain of the patient is detected with a gamma emission detector.

3. The method of claim 1 wherein the tin-117m has a specific activity between 800 Ci/g and 20,000 Ci/g at the end of bombardment.

4. The method of claim 1 wherein the tin-117m has a specific activity between 1,000 Ci/g and 5,000 Ci/g at the end of bombardment.

5. The method of claim 1 wherein annexin V labeled with a detectable radionuclide includes a linking molecule, wherein the linking molecule is 1,4,7,10-tetraazacyclododecane-1,4,7,10-tetraacetic acid ("DOTA").

* * * * *

UNITED STATES PATENT AND TRADEMARK OFFICE
CERTIFICATE OF CORRECTION

PATENT NO. : 10,286,093 B2
APPLICATION NO. : 14/891835
DATED : May 14, 2019
INVENTOR(S) : Gilbert R. Gonzales et al.

Page 1 of 2

It is certified that error appears in the above-identified patent and that said Letters Patent is hereby corrected as shown below:

In the Specification

| | | |
|---|---|---|
| Column 1, Lines 5-10, Priority Claim, "This application is based on" | should read | --This application is a submission under 35 USC § 371 of International Application No. PCT/US2014/038933, filed May 21, 2014, which is based on-- |
| Column 1, Lines 23-24, "up the 50% of the brain mass" | should read | --up to 50% of the brain mass-- |
| Column 2, Line 17, "has a specific activity may range" | should read | --has a specific activity range-- |
| Column 2, Line 19-20, "has a specific activity may range" | should read | --has a specific activity range-- |
| Column 2, Line 22, "has a specific activity may range" | should read | --has a specific activity range-- |
| Column 2, Lines 45-46, "one of its amino acids provide" | should read | --one of its amino acids provides-- |
| Column 3, Line 34, "Alzheimer's disease because | should read | --Alzheimer's disease. Because-- |
| Column 3, Line 45, "annexin A1 can b readministered" | should read | --annexin A1 can be readministered-- |
| Column 4, Line 13, "aqueous solution f a bifunctional" | should read | --aqueous solution of a bifunctional-- |

Signed and Sealed this
Twenty-second Day of October, 2019

Andrei Iancu
*Director of the United States Patent and Trademark Office*

CERTIFICATE OF CORRECTION (continued)
U.S. Pat. No. 10,286,093 B2

Column 4, Lines 23-24, "was adjusted to out then"    should read    --was adjusted to about 6 then--

Column 4, Line 51, "a hormesis affect is achieved."    should read    --a hormesis effect is achieved.--